United States Patent

Toida et al.

[11] Patent Number: 5,961,449
[45] Date of Patent: Oct. 5, 1999

[54] GLUCOSE CONCENTRATION MEASURING METHOD AND APPARATUS

[75] Inventors: Masahiro Toida; Ichirou Miyagawa, both of Kanagawa-ken, Japan

[73] Assignee: Fuji Photo Film Co., Ltd., Kanagawa-ken, Japan

[21] Appl. No.: 09/138,124

[22] Filed: Aug. 24, 1998

Related U.S. Application Data

[62] Division of application No. 08/857,205, May 15, 1997.

[30] Foreign Application Priority Data

May 16, 1996  [JP]  Japan ................................ 8-121790

[51] Int. Cl.[6] ....................................................... A61B 5/00
[52] U.S. Cl. .............................................................. 600/319
[58] Field of Search ................................... 600/316, 318, 600/319

[56] References Cited

U.S. PATENT DOCUMENTS 3,958,560  5/1976  March .
5,025,758  6/1991  Weiss .
5,209,231  5/1993  Cote et al. .
5,433,197  7/1995  Stark .
5,459,570  10/1995  Swanson et al. .
5,535,743  7/1996  Backhaus et al. .
5,553,617  9/1996  Barkenhagen ............................ 600/318

Primary Examiner—Eric F. Winakur
Attorney, Agent, or Firm—Sughrue, Mion, Zinn, Macpeak & Seas, PLLC

[57] ABSTRACT

A low coherence light beam is irradiated to the eyeball. A backward scattered light beam, which is reflected from each depth position in the eyeball, and a reference light beam, which is reflected from a mirror capable of moving, are caused to interfere with each other. A first backward scattered light beam, which comes from the interface between the cornea and the anterior aqueous chamber, and a second backward scattered light beam, which comes from the interface between the anterior aqueous chamber and the crystalline lens, are thus separated accurately from each other. An optical absorbance of the anterior aqueous chamber (the aqueous humor) is calculated from the intensities of the two backward scattered light beams. Each of a plurality of low coherence light beams having different wavelengths is irradiated to the eyeball, and the aforesaid operation is repeated. The concentration of glucose in the aqueous humor is measured by utilizing near-infrared spectroscopy. The measurement is thus achieved non-invasively and accurately.

8 Claims, 7 Drawing Sheets

F I G . 2
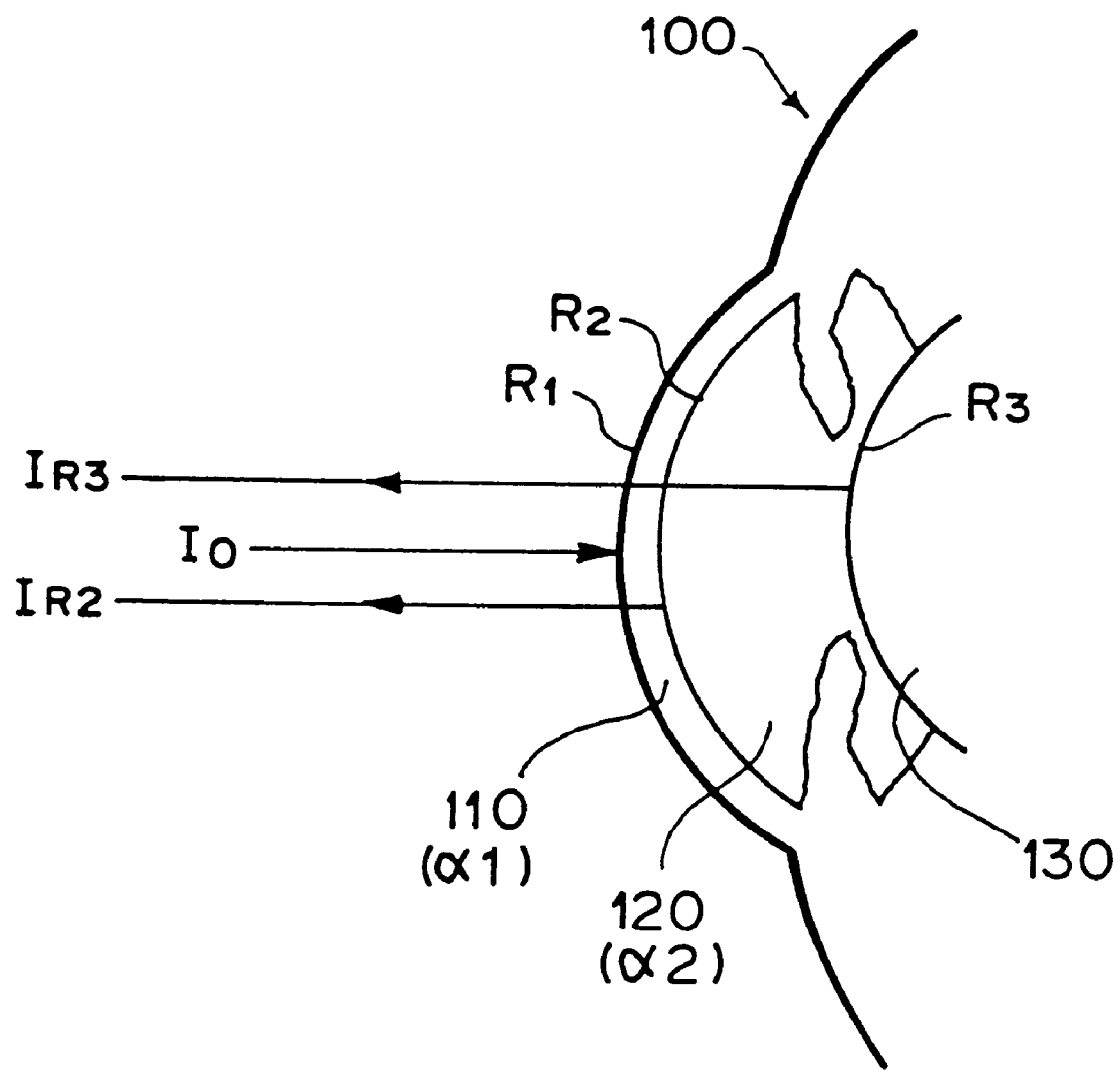

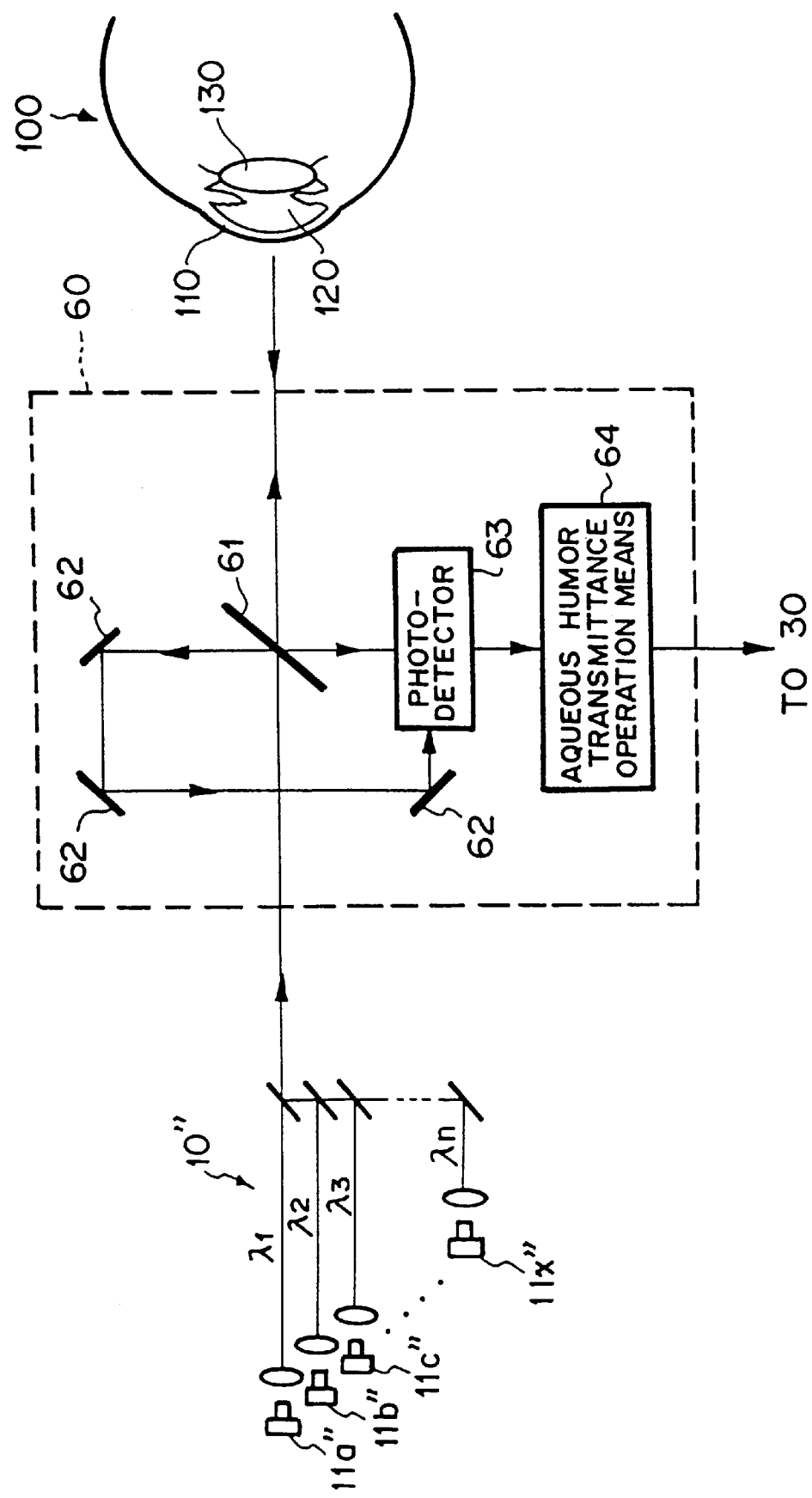
F I G. 7

GLUCOSE CONCENTRATION MEASURING METHOD AND APPARATUS

This is a divisional of application Ser. No. 08/857,205 filed May 15, 1997.

BACKGROUND OF THE INVENTION

1. Field of the Invention

This invention relates to a method and apparatus for measuring a concentration of glucose in a living body. This invention particularly relates to a method and apparatus for measuring non-invasively the concentration of glucose in the aqueous humor in the anterior aqueous chamber of the eyeball, and a method and apparatus for measuring non-invasively the concentration of glucose in the blood in accordance with the concentration of glucose in the aqueous humor.

2. Description of the Prior Art

The mean level of glucose in the blood varies for different persons and is an important index for determining whether drugs are to be or are not to be administered to diabetic patients.

The concentration of glucose in the blood has the characteristics such that it fluctuates markedly within a very short time in accordance with food intake, physical activity, a complication by another disease, or the like. Urgent dosage is often required due to a sharp increase in concentration of blood glucose.

Therefore, as for patients having such a disease, it is desired that the concentration of glucose in the blood can be monitored at as short intervals as possible. Ordinarily, monitoring of the concentration of glucose in the blood is carried out by lancing the finger of the patient in order to obtain a drop of blood, analyzing the drop of blood, and thereby measuring the concentration of glucose in the blood. Since the lancing of the finger is painful, it is difficult to compel the patients to undergo the measurement procedure many times per day.

Accordingly, recently, in lieu of the invasive measurements having the drawbacks described above, various non-invasive measuring methods, which are not accompanied by pain, have been proposed.

The non-invasive measuring methods are primarily based upon the findings in that the concentration of glucose in the aqueous humor, which fills the anterior aqueous chamber located between the cornea and the crystalline lens of the human eyeball, has strong correlation with the concentration of glucose in the blood, though the level of correlation varies for different persons. With the non-invasive measuring methods, the concentration of glucose in the aqueous humor is measured non-invasively.

For example, a glucose sensor system, wherein the angle of rotation of infrared radiation having impinged upon the aqueous humor is measured, and the concentration of glucose having relationship with the angle of rotation is thereby determined, is proposed in, for example, U.S. Pat. No. 3,958,560.

Also, a technique for measuring stimulated Raman light from glucose is disclosed in, for example, WO 92/10131.

Further, a device for measuring the optical properties of light reflected from the crystalline lens of the eye is described in, for example, U.S. Pat. No. 5,535,743. Furthermore, a method for measuring the concentration of glucose in the aqueous humor is described in, for example, U.S. Pat. No. 5,433,197.

However, with the device described in U.S. Pat. No. 5,535,743, light reflected from the interface between the cornea and the aqueous humor cannot be eliminated, and information representing absorption at the cornea is detected together with the necessary information. Therefore, the accuracy, with which the concentration of glucose in the aqueous humor is determined, cannot be kept high.

Further, in U.S. Pat. No. 5,535,743, nothing is disclosed as to technical means to be used for measuring a minute change in absorbance. Therefore, the device described in U.S. Pat. No. 5,535,743 cannot be appropriately used in practice.

As for the glucose sensor system proposed in U.S. Pat. No. 3,958,560, many compounds other than glucose in the aqueous humor are optically active and take part in rotation of the plane of polarization. Also, the cornea exhibits birefringence and therefore causes rotation of the plane of polarization to occur. Accordingly, with the glucose sensor system proposed in U.S. Pat. No. 3,958,560, wherein the concentration of glucose in the aqueous humor is determined from the angle of rotation, the measurement accuracy cannot be kept high.

With the technique disclosed in WO 92/10131, in order for stimulated Raman light from glucose to be measured, a pump laser beam having a high intensity is introduced into the anterior aqueous chamber and in a direction normal to the vision line optical axis. Therefore, a practical measuring system cannot be constituted easily.

SUMMARY OF THE INVENTION

The primary object of the present invention is to provide a glucose concentration measuring method, wherein the concentration of glucose in the aqueous humor is measured non-invasively and with a high accuracy.

Another object of the present invention is to provide a glucose concentration measuring method, wherein the concentration of glucose in the blood is measured non-invasively from the non-invasively obtained concentration of glucose in the aqueous humor.

Another object of the present invention is to provide an apparatus for carrying out the glucose concentration measuring method.

The present invention provides a first glucose concentration measuring method, comprising the steps of:

i) splitting a low coherence light beam, which has been radiated out of a predetermined light source, into a signal light beam and a reference light beam, each of which travels along one of two different optical paths, ii) modulating at least either one of the signal light beam and the reference light beam such that a slight difference in frequency may occur between them, iii) irradiating the signal light beam to the eyeball lying at a predetermined position, iv) causing a first backward scattered light beam of the signal light beam having been irradiated to the eyeball, the first backward scattered light beam coming from an interface between the cornea and the anterior aqueous chamber of the eyeball, and the reference light beam to interfere with each other by adjusting an optical path length of the reference light beam, a first interference light beam being thereby obtained, v) measuring an intensity of the first interference light beam, vi) calculating an intensity of the first backward scattered light beam from the intensity of the first interference light beam, vii) causing a second backward scattered light beam of the signal light beam having been irradiated to the eyeball, the second backward scattered light beam coming from an interface between the anterior aqueous chamber and the crystalline lens of the eyeball, and the reference light beam to interfere with each other by adjusting the optical path length of the reference light beam, a second interference light beam being thereby obtained, viii) measuring an intensity of the second interference light beam, ix) calculating an intensity of the second backward scattered light beam from the intensity of the second interference light beam, x) obtaining light absorption characteristics of constituents of the aqueous humor, which fills the anterior aqueous chamber, from the intensity of the first backward scattered light beam and the intensity of the second backward scattered light beam, xi) obtaining light absorption characteristics of the constituents of the aqueous humor with respect to each of a plurality of other low coherence light beams, which are of wavelength bands different from the wavelength band of the low coherence light beam, in the same manner, and xii) calculating a concentration of glucose in the constituents of the aqueous humor from the light absorption characteristics, which have been obtained with respect to the plurality of the low coherence light beams.

In the first glucose concentration measuring method in accordance with the present invention, as the light source for producing each of the low coherence light beams, a superluminescent diode (SLD), a light emitting diode (LED), or the like, which produces a light beam having a coherence length of as short as approximately several tens of microns, may be employed. Practically, an SLD having a high directivity should preferably be used.

The term "measuring an intensity of an interference light beam" as used herein means the measurement of the intensity of the beat signal (i.e., the interference light beam), the intensity of which repeatedly becomes high and low at a frequency equal to the difference between the frequencies of the backward scattered light beam (i.e., the signal light beam) and the reference light beam.

In the first glucose concentration measuring method in accordance with the present invention, each of the low coherence light beams may be selected as a portion of light, which is of an emission wavelength band wider than the wavelength band of each low coherence light beam. Alternatively, each of the low coherence light beams may be radiated out of one of a plurality of different light sources.

In cases where a plurality of different light sources, which produce the low coherence light beams of different wavelength bands, are employed, the low coherence light beams may be radiated successively out of the plurality of the light sources, and the interference light beams corresponding to the low coherence light beams may be detected with a single photodetector.

The present invention also provides a second glucose concentration measuring method, comprising the steps of:

i) splitting a coherent light beam (e.g., a laser beam), which has been radiated out of a predetermined light source and the frequency of which is swept temporally in a sawtooth-like form (e.g., as illustrated in FIG. 6), into a signal light beam and a reference light beam, each of which travels along one of two different optical paths, ii) irradiating the signal light beam to the eyeball lying at a predetermined position, iii) causing a first backward scattered light beam of the signal light beam, the first backward scattered light beam coming from an interface between the cornea and the anterior aqueous chamber of the eyeball, and the reference light beam to interfere with each other, the reference light beam being constituted of the coherent light beam, which has been radiated out of the light source with a difference in time in accordance with a difference between an optical path length of the signal light beam (traveling from the position, at which the signal light beam is split from the reference light beam, to the interface between the cornea and the anterior aqueous chamber of the eyeball) and the first backward scattered light beam (traveling from the interface between the cornea and the anterior aqueous chamber of the eyeball to the position, at which the first backward scattered light beam interferes with the reference light beam) and an optical path length of the reference light beam (traveling from the position, at which the reference light beam is split from the signal light beam, to the position, at which the reference light beam interferes with the first backward scattered light beam), and which has a difference in frequency with respect to the first backward scattered light beam, a first interference light beam being thereby obtained, iv) measuring an intensity of the first interference light beam, v) calculating an intensity of the first backward scattered light beam from the intensity of the first interference light beam, vi) causing a second backward scattered light beam of the signal light beam, the second backward scattered light beam coming from an interface between the anterior aqueous chamber and the crystalline lens of the eyeball, and the reference light beam to interfere with each other, the reference light beam being constituted of the coherent light beam, which has been radiated out of the light source with a difference in time in accordance with a difference between an optical path length of the signal light beam (traveling from the position, at which the signal light beam is split from the reference light beam, to the interface between the anterior aqueous chamber and the crystalline lens of the eyeball) and the second backward scattered light beam (traveling from the interface between the anterior aqueous chamber and the crystalline lens of the eyeball to the position, at which the second backward scattered light beam interferes with the reference light beam) and an optical path length of the reference light beam (traveling from the position, at which the reference light beam is split from the signal light beam, to the position, at which the reference light beam interferes with the second backward scattered light beam), and which has a difference in frequency with respect to the second backward scattered light beam, a second interference light beam being thereby obtained, vii) measuring an intensity of the second interference light beam, viii) calculating an intensity of the second backward scattered light beam from the intensity of the second interference light beam, ix) obtaining light absorption characteristics of constituents of the aqueous humor, which fills the anterior aqueous chamber, from the intensity of the first backward scattered light beam and the intensity of the second backward scattered light beam, x) obtaining light absorption characteristics of the constituents of the aqueous humor with respect to each of a plurality of other coherent light beams, which have wavelengths different from the wavelength of the coherent light beam, in the same manner, and xi) calculating a concentration of glucose in the constituents of the aqueous humor from the light absorption characteristics, which have been obtained with respect to the plurality of the coherent light beams.

In the second glucose concentration measuring method in accordance with the present invention, the reference light beam, which is caused to interfere with the first backward scattered light beam, has a difference in frequency with respect to the first backward scattered light beam. The reasons for this will be described hereinbelow.

The optical paths are set such that the sum of the length of the optical path, along which the signal light beam travels, and the length of the optical path, along which the first backward scattered light beam travels, may be different from the length of the optical path, along which the reference light beam travels. (The optical path length of the reference light beam may be shorter than the sum of the optical path lengths of the signal light beam and the first backward scattered light beam. Alternatively, the optical path length of the reference light beam may be longer than the sum of the optical path lengths of the signal light beam and the first backward scattered light beam.) Due to the difference in optical path length, for example, in cases where the optical path length of the reference light beam is shorter than the sum of the optical path lengths of the signal light beam and the first backward scattered light beam, the reference light beam arrives at the position, at which the wavefront matching (the interference) is effected, with an earlier timing than the first backward scattered light beam does.

Specifically, at the time at which the first backward scattered light beam arrives at the position of interference, the reference light beam, which was split from the signal light beam that formed the first backward scattered light beam, has already passed through the position of interference, and the reference light beam, which is a portion of the coherent light beam radiated out of the light source with a later timing than the signal light beam was, arrives at the position of interference.

The frequency of the coherent light beam, which is radiated out of the light source with a later timing than the signal light beam was, is swept temporally. Therefore, there is a slight difference in frequency between the reference light beam, which is caused to interfere with the first backward scattered light beam, and the first backward scattered light beam.

The reference light beam, which is caused to interfere with the second backward scattered light beam, has a frequency different from the frequency of the reference light beam, which is caused to interfere with the first backward scattered light beam. Specifically, the first backward scattered light beam comes from the interface between the cornea and the anterior aqueous chamber, and the second backward scattered light beam comes from the interface between the anterior aqueous chamber and the crystalline lens, the latter interface being located at a position in the eyeball deeper than the former interface. Therefore, a difference in time, which corresponds to the difference in optical path length between the first backward scattered light beam and the second backward scattered light beam (the difference being two times as long as the thickness of the anterior aqueous chamber), occurs between when the first backward scattered light beam arrives at the position of interference and when the second backward scattered light beam arrives as the position of interference. As a result, the reference light beam, which is caused to interfere with the second backward scattered light beam, is the one constituted of a portion of the coherent light beam, which is radiated out of the light source with a later timing than the reference light beam caused to interfere with the first backward scattered light beam is.

In the second glucose concentration measuring method in accordance with the present invention, the coherent light beams may be selectively radiated out of a single light source. Alternatively, each of the coherent light beams may be radiated out of one of a plurality of different light sources.

The present invention further provides a third glucose concentration measuring method, comprising the steps of:

i) irradiating an ultrashort pulsed light beam, which has been radiated out of a predetermined light source, to the eyeball, ii) measuring each of an intensity of a first backward scattered light beam of the ultrashort pulsed light beam, the first backward scattered light beam coming from an interface between the cornea and the anterior aqueous chamber of the eyeball, and an intensity of a second backward scattered light beam of the ultrashort pulsed light beam, the second backward scattered light beam coming from an interface between the anterior aqueous chamber and the crystalline lens of the eyeball, iii) obtaining light absorption characteristics of constituents of the aqueous humor, which fills the anterior aqueous chamber, from the intensity of the first backward scattered light beam and the intensity of the second backward scattered light beam, iv) obtaining light absorption characteristics of the constituents of the aqueous humor with respect to each of a plurality of other ultrashort pulsed light beams, which have wavelengths different from the wavelength of the ultrashort pulsed light beam, in the same manner, and v) calculating a concentration of glucose in the constituents of the aqueous humor from the light absorption characteristics, which have been obtained with respect to the plurality of the ultrashort pulsed light beams having different wavelengths.

The term "ultrashort pulsed light beam" as used herein means the pulsed light beam, which is emitted for a very short time (e.g., on the order of femtoseconds to picoseconds) such that the intensity of the first backward scattered light beam and the intensity of the second backward scattered light beam coming from the interface between the anterior aqueous chamber and the crystalline lens can at least be separated temporally and measured respectively. The ultrashort pulsed light beam may be produced by a mode locked Ti:sapphire laser, or the like. In cases where the ultrashort pulsed light beam is employed, the second backward scattered light beam, which lags behind the first backward scattered light beam by a length of time corresponding to the distance two times as long as the thickness of the anterior aqueous chamber, can be detected separately from the first backward scattered light beam by using a photodetector capable of effecting time resolution, such as a streak camera.

In the third glucose concentration measuring method in accordance with the present invention, the ultrashort pulsed light beams may be selectively radiated out of a single light source. Alternatively, each of the ultrashort pulsed light beams may be radiated out of one of a plurality of different light sources.

The present invention still further provides a fourth glucose concentration measuring method, comprising the steps of:

with respect to concentrations of glucose in the constituents of the aqueous humor, which concentrations have been measured with the aforesaid first, second, or third glucose concentration measuring method in accordance with the present invention, invasively measuring the corresponding concentrations of glucose in the blood, correlation between the concentrations of glucose in the constituents of the aqueous humor and the concentrations of glucose in the blood being thereby determined previously, and thereafter non-invasively determining a concentration of glucose in the blood from a concentration of glucose in the constituents of the aqueous humor, which concentration is newly measured with the aforesaid first, second, or third glucose concentration measuring method in accordance with the present invention, and the correlation.

The present invention also provides an apparatus for carrying out the aforesaid first glucose concentration measuring method in accordance with the present invention. Specifically, the present invention also provides a first glucose concentration measuring apparatus, comprising:

i) a light source device for radiating out a plurality of low coherence light beams, which are of different emission wavelength bands, ii) an optical path splitting means for splitting each of the low coherence light beams, which has been radiated out of the light source device, into a signal light beam irradiated to the eyeball and a reference light beam, each of which travels along one of two different optical paths, iii) a modulation means, which is located in at least either one of the two different optical paths and modulates at least either one of the signal light beam and the reference light beam such that a slight difference in frequency may occur between them, iv) an optical path length adjusting means for adjusting the length of the optical path, along which the reference light beam travels, v) a wavefront matching means for:

matching a wave front of a first backward scattered light beam of the signal light beam having been irradiated to the eyeball, the first backward scattered light beam coming from an interface between the cornea and the anterior aqueous chamber of the eyeball, and a wave front of the reference light beam with each other, and matching a wave front of a second backward scattered light beam of the signal light beam having been irradiated to the eyeball, the second backward scattered light beam coming from an interface between the anterior aqueous chamber and the crystalline lens of the eyeball, and a wave front of the reference light beam with each other, vi) a photodetector for photoelectrically detecting an intensity of a first interference light beam, which is obtained from the matching of the wave front of the first backward scattered light beam and the wave front of the reference light beam with each other, and an intensity of a second interference light beam, which is obtained from the matching of the wave front of the second backward scattered light beam and the wave front of the reference light beam with each other, vii) a heterodyne operation means for calculating an intensity of the first backward scattered light beam from the intensity of the first interference light beam, and calculating an intensity of the second backward scattered light beam from the intensity of the second interference light beam, viii) a light absorption characteristics analyzing means for obtaining light absorption characteristics of constituents of the aqueous humor, which fills the anterior aqueous chamber, from the intensity of the first backward scattered light beam and the intensity of the second backward scattered light beam, and ix) a glucose concentration calculating means for calculating a concentration of glucose in the constituents of the aqueous humor from the light absorption characteristics, which have been obtained with respect to the plurality of the low coherence light beams.

In the first glucose concentration measuring apparatus in accordance with the present invention, the light source device may comprise a single light source for radiating out low coherence light, which is of an emission wavelength band wider than the wavelength band of each of the low coherence light beams, and a wavelength selecting means for selecting each of the low coherence light beams with respect to the wavelength from the low coherence light, which is of the wide emission wavelength band. Alternatively, the light source device may comprise a plurality of light sources, each of which radiates out one of the low coherence light beams.

The present invention further provides an apparatus for carrying out the aforesaid second glucose concentration measuring method in accordance with the present invention. Specifically, the present invention further provides a second glucose concentration measuring apparatus, comprising:

i) a light source device for radiating out a plurality of coherent light beams, which have different wavelengths and the frequencies of which are swept temporally in a sawtooth-like form (e.g., as illustrated in FIG. 6), ii) an optical path splitting means for splitting each of the coherent light beams, which has been radiated out of the light source device and the frequency of which is swept, into a signal light beam irradiated to the eyeball and a reference light beam, each of which travels along one of two different optical paths, iii) a wavefront matching means for:

matching a wave front of a first backward scattered light beam of the signal light beam, the first backward scattered light beam coming from an interface between the cornea and the anterior aqueous chamber of the eyeball, and a wave front of the reference light beam with each other, the reference light beam being constituted of the coherent light beam, which has been radiated out of the light source device with a difference in time in accordance with a difference between an optical path length of the signal light beam and the first backward scattered light beam and an optical path length of the reference light beam, and which has a difference in frequency with respect to the first backward scattered light beam, and matching a wave front of a second backward scattered light beam of the signal light beam, the second backward scattered light beam coming from an interface between the anterior aqueous chamber and the crystalline lens of the eyeball, and a wave front of the reference light beam with each other, the reference light beam being constituted of the coherent light beam, which has been radiated out of the light source device with a difference in time in accordance with a difference between an optical path length of the signal light beam and the second backward scattered light beam and an optical path length of the reference light beam, and which has a difference in frequency with respect to the second backward scattered light beam, iv) a photodetector for photoelectrically detecting an intensity of a first interference light beam, which is obtained from the matching of the wave front of the first backward scattered light beam and the wave front of the reference light beam, the reference light beam having the slight difference in frequency with respect to the first backward scattered light beam, with each other, and an intensity of a second interference light beam, which is obtained from the matching of the wave front of the second backward scattered light beam and the wave front of the reference light beam, the reference light beam having the slight difference in frequency with respect to the second backward scattered light beam, with each other, v) a heterodyne operation means for calculating an intensity of the first backward scattered light beam from the intensity of the first interference light beam, and calculating an intensity of the second backward scattered light beam from the intensity of the second interference light beam, vi) a light absorption characteristics analyzing means for obtaining light absorption characteristics of constituents of the aqueous humor, which fills the anterior aqueous chamber, from the intensity of the first backward scattered light beam and the intensity of the second backward scattered light beam, and vii) a glucose concentration calculating means for calculating a concentration of glucose in the constituents of the aqueous humor from the light absorption characteristics, which have been obtained with respect to the plurality of the coherent light beams.

In the second glucose concentration measuring apparatus in accordance with the present invention, the light source device may comprise a single light source capable of selectively radiating out each of the plurality of the coherent light beams, and a control means for controlling the light source such that the light source may selectively radiate out one of the plurality of the coherent light beams. Alternatively, the light source device may comprise a plurality of light sources, each of which radiates out one of the coherent light beams.

The present invention still further provides an apparatus for carrying out the aforesaid third glucose concentration measuring method in accordance with the present invention. Specifically, the present invention still further provides a third glucose concentration measuring apparatus, comprising:

i) a light source device for radiating out a plurality of ultrashort pulsed light beams, which have different wavelengths, ii) an optical time-domain backward scattering measurement means for irradiating the ultrashort pulsed light beam to the eyeball, and carrying out time series measurement of each of an intensity of a first backward scattered light beam of the ultrashort pulsed light beam, the first backward scattered light beam coming from an interface between the cornea and the anterior aqueous chamber of the eyeball, and an intensity of a second backward scattered light beam of the ultrashort pulsed light beam, the second backward scattered light beam coming from an interface between the anterior aqueous chamber and the crystalline lens of the eyeball, iii) a light absorption characteristics analyzing means for obtaining light absorption characteristics of constituents of the aqueous humor, which fills the anterior aqueous chamber, from the intensity of the first backward scattered light beam and the intensity of the second backward scattered light beam, and iv) a glucose concentration calculating means for calculating a concentration of glucose in the constituents of the aqueous humor from the light absorption characteristics, which have been obtained with respect to the plurality of the ultrashort pulsed light beams having different wavelengths.

In the third glucose concentration measuring apparatus in accordance with the present invention, the light source device may comprise a single light source capable of selectively radiating out each of the plurality of the ultrashort pulsed light beams, and a control means for controlling the light source such that the light source may selectively radiate out one of the plurality of the ultrashort pulsed light beams. Alternatively, the light source device may comprise a plurality of light sources, each of which radiates out one of the ultrashort pulsed light beams.

The present invention also provides a fourth glucose concentration measuring apparatus, comprising a table representing correlation between concentrations of glucose in the constituents of the aqueous humor, which concentrations have been measured with the aforesaid first, second, or third glucose concentration measuring apparatus in accordance with the present invention, and concentrations of glucose in the blood, which have been measured previously, wherein a concentration of glucose in the blood is non-invasively determined from a concentration of glucose in the constituents of the aqueous humor, which concentration is newly measured with the aforesaid first, second, or third glucose concentration measuring apparatus in accordance with the present invention, and the table.

With the first and second glucose concentration measuring methods and the first and second glucose concentration measuring apparatuses in accordance with the present invention, wherein the optical heterodyne backward scattering measurement technique is employed, each of an intensity $I_{R2}$ of the weak first backward scattered light beam of the incident light beam, the first backward scattered light beam coming from the interface between the cornea and the anterior aqueous chamber, and an intensity $I_{R3}$ of the weak second backward scattered light beam of the incident light beam, the second backward scattered light beam coming from the interface between the anterior aqueous chamber and the crystalline lens, can be detected accurately.

As illustrated in FIG. 2, the intensity of the incident light beam impinging upon the eyeball is represented by $I_0$. The reflectivity of the interface between air and the cornea is represented by $R_1$, the reflectivity of the interface between the cornea and the anterior aqueous chamber is represented by $R_2$, and the reflectivity of the interface between the anterior aqueous chamber and the crystalline lens is represented by $R_3$. Also, the optical absorbance of the cornea with respect to the incident light beam along one way of the optical path is represented by $\alpha_1$, and the optical absorbance of the anterior aqueous chamber (the aqueous humor) with respect to the incident light beam along one way of the optical path is represented by $\alpha_2$. In such cases, the intensity $I_{R2}$ of the first backward scattered light beam and the intensity $I_{R3}$ of the second backward scattered light beam may be represented by Formulas (1) and (2) shown below.

$$I_{R2}=I_0(1-R_1)^2 R_2(1-\alpha_1)^2 \quad (1)$$

$$I_{R3}=I_0(1-R_1)^2(1-R_2)^2 R_3(1-\alpha_1)^2(1-\alpha_2)^2 \quad (2)$$

The ratio ($I_{R3}/I_{R2}$) of the intensity $I_{R3}$ of the second backward scattered light beam to the intensity $I_{R2}$ of the first backward scattered light beam, each intensity having been detected accurately, may be represented by Formula (3) shown below.

$$I_{R3}/I_{R2}=(R_3/R_2)(1-R_2)^2(1-\alpha_2)^2 \quad (3)$$

Since $I_{R3}$, $I_{R2}$, $R_3$ and $R_2$ are already known, the optical absorbance $\alpha_2$ of the aqueous humor with respect to the incident light beam along one way of the optical path can be calculated from them.

Besides glucose, the aqueous humor contains a plurality of other constituents, such as NaCl. Therefore, the operation described above is carried out repeatedly for a plurality of the incident light beams having different wavelengths, and known near-infrared spectroscopy including a multivariate analysis is utilized. In this manner, the concentration of glucose alone in the aqueous humor can be determined.

For each patient, the correlation between the concentrations of glucose in the aqueous humor, which have thus been obtained non-invasively, and the concentrations of glucose in the blood, which have been obtained invasively in accordance with the conventional procedure, is prepared as, for example, a conversion table. After the correlation is prepared, the concentration of glucose in the blood need not be measured, and only the concentration of glucose in the aqueous humor may be measured non-invasively. Therefore, measurements can be made at a high repeatability without giving the patient pain.

With the third glucose concentration measuring method and the third glucose concentration measuring apparatus in accordance with the present invention, as illustrated in FIG. 8, the intensity of the first backward scattered light beam and the intensity of the second backward scattered light beam can be measured respectively such that they may be separated temporally. The amounts of the first backward scattered light beam and the second backward scattered light beam, i.e. $I_{R2}$ of Formula (1) shown above and $I_{R3}$ of Formula (3) shown above, can be calculated by integrating the corresponding wave forms shown in FIG. 8 with respect to time.

Therefore, the optical absorbance $\alpha_2$ of the aqueous humor with respect to the incident light beam along one way of the optical path can be calculated with Formula (3) shown above.

Also, as in the aforesaid glucose concentration measuring methods and apparatuses in accordance with the present invention, the operation described above is carried out repeatedly for a plurality of the incident light beams having different wavelengths, and known near-infrared spectroscopy including a multivariate analysis is utilized. In this manner, the concentration of glucose alone in the aqueous humor can be determined.

BRIEF DESCRIPTION OF THE DRAWINGS

FIG. 2 is an explanatory view showing relationship between an incident light beam impinging upon the eyeball and backward scattered light beams, FIG. 7 is a schematic view showing an embodiment of an apparatus for carrying out the third glucose concentration measuring method in accordance with the present invention.

DESCRIPTION OF THE PREFERRED EMBODIMENTS

The present invention will hereinbelow be described in further detail with reference to the accompanying drawings.

Figure 1:
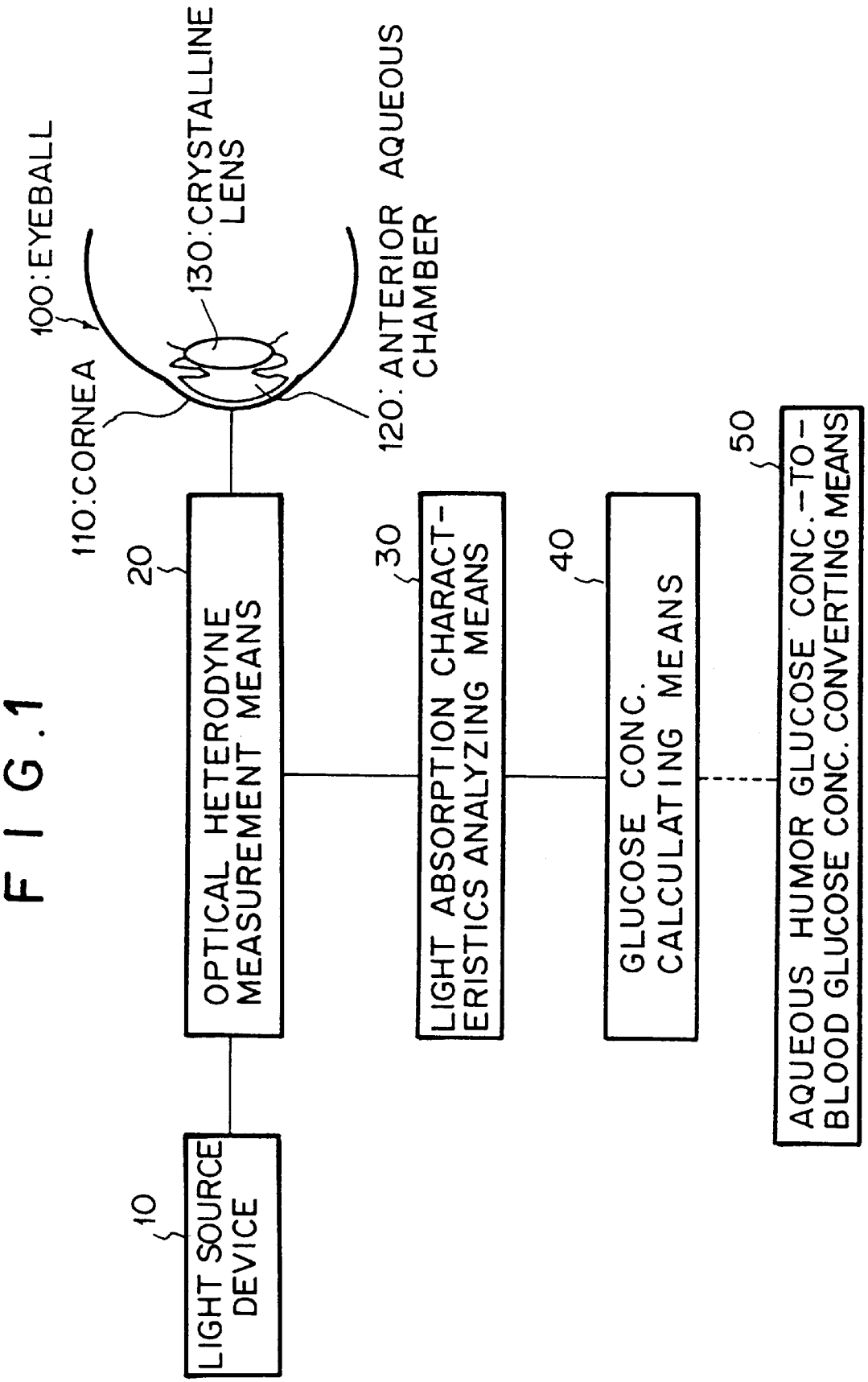
FIG. 1 is a block diagram showing a fundamental constitution of an apparatus for carrying out the first glucose concentration measuring method in accordance with the present invention.

FIG. 1 shows a fundamental constitution of an apparatus for carrying out the first glucose concentration measuring method in accordance with the present invention.

With reference to FIG. 1, the glucose concentration measuring apparatus comprises a light source device 10 for radiating out low coherence light beams, which are of a plurality of different wavelength bands and have a coherence length on the order of several tens of microns. The glucose concentration measuring apparatus also comprises an optical heterodyne measurement means 20 for irradiating the low coherence light beam, which has been radiated out of the light source device 10, to the eyeball 100, and measuring the intensity of a first backward scattered light beam of the incident light beam, the first backward scattered light beam coming from the interface between the cornea 110 and the anterior aqueous chamber 120 of the eyeball 100, and the intensity of a second backward scattered light beam of the incident light beam, the second backward scattered light beam coming from the interface between the anterior aqueous chamber 120 and the crystalline lens 130 of the eyeball 100, with an optical heterodyne backward scattering measurement technique. The glucose concentration measuring apparatus further comprises a light absorption characteristics analyzing means 30 for obtaining an optical absorbance of constituents of the aqueous humor, which fills the anterior aqueous chamber 120, with respect to the incident light beam, which has a certain wavelength, in accordance with the intensity of the first backward scattered light beam and the intensity of the second backward scattered light beam. The glucose concentration measuring apparatus still further comprises a glucose concentration calculating means 40 for calculating a concentration of glucose in the constituents of the aqueous humor from a plurality of optical absorbances, which have been obtained respectively for the light beams of different wavelengths having been radiated out of the light source device 10, by utilizing known near-infrared spectroscopy including multivariate analysis.

Figure 3:
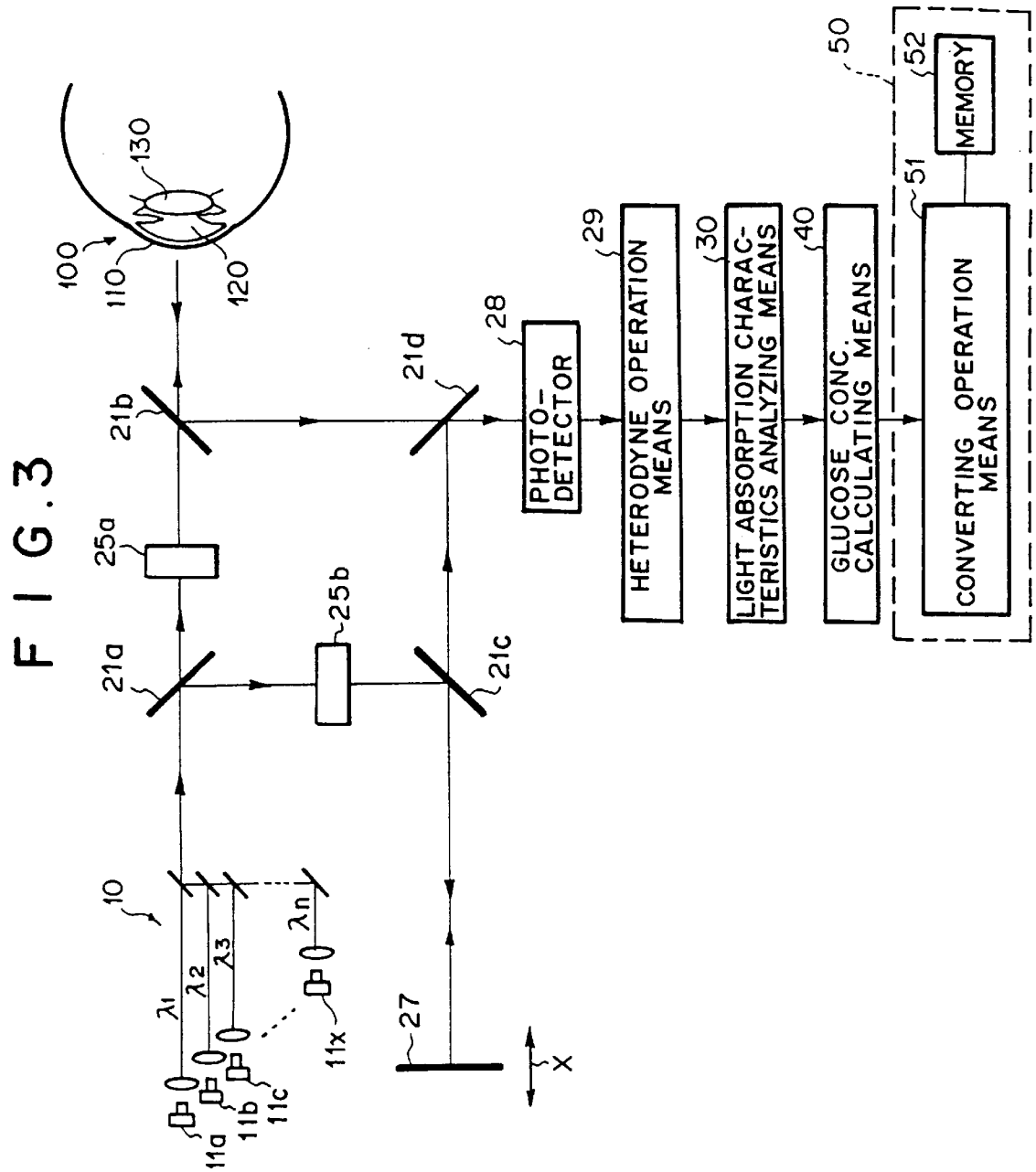
FIG. 3 is a schematic view showing an embodiment of the apparatus for carrying out the first glucose concentration measuring method in accordance with the present invention.

FIG. 3 shows an embodiment of the apparatus of FIG. 1 for carrying out the first glucose concentration measuring method in accordance with the present invention.

As the light source device 10 shown in FIG. 1, the glucose concentration measuring apparatus of FIG. 3 comprises a plurality of light sources, i.e. an SLD 11a for radiating out a low coherence light beam, which is of abroad wavelength band and has a center wavelength of λ1, an SLD 11b for radiating out a low coherence light beam, which is of a broad wavelength band and has a center wavelength of λ2, ..., an SLD 11x for radiating out a low coherence light beam, which is of a broad wavelength band and has a center wavelength of λn. Also, in the glucose concentration measuring apparatus of FIG. 3, the optical heterodyne measurement means 20 shown in FIG. 1 comprises four beam splitters 21a, 21b, 21c, and 21d for splitting each of the low coherence light beams, which has been radiated out of the light source device 10, into a signal light beam and a reference light beam, each of which travels along one of two different optical paths, and matching the wave fronts of the two light beams with each other. The optical heterodyne measurement means 20 also comprises acousto-optic modulators 25a and 25b for respectively modulating the signal light beam and the reference light beam such that a slight difference in frequency Δf may occur between the two light beams, and a reflection mirror 27, which can move along the optical axis direction and adjusts the length of the optical path, along which the reference light beam travels. The optical heterodyne measurement means 20 further comprises a photodetector 28 for detecting an intensity of an interference light beam, which is obtained from the matching of the wave front of a backward scattered light beam of the signal light beam having been guided to the eyeball 100 and the wave front of the reference light beam with each other. The optical heterodyne measurement means 20 still further comprises a heterodyne operation means 29 for calculating an intensity of the backward scattered light beam from the intensity of the interference light beam by utilizing the optical heterodyne backward scattering measurement technique.

The SLDs 11a, 11b, ..., 11x successively radiate out the low coherence light beams. As for the modulation, both of the signal light beam and the reference light beam need not necessarily be modulated as in this embodiment. It is sufficient for at least either one of the signal light beam and the reference light beam to be modulated such that a slight difference in frequency may occur between the two light beams.

How this embodiment of the glucose concentration measuring apparatus in accordance with the present invention operates will be described hereinbelow.

Firstly, the SLD 11a radiates out the low coherence light beam, which has a center wavelength of λ1. At this time, the other light sources do not radiate out the light beams. The low coherence light beam having been radiated out of the SLD 11a is split by the first beam splitter 21a, which is located in the optical path, into the signal light beam and the reference light beam. The signal light beam and the reference light beam are respectively modulated by the acousto-optic modulators 25a and 25b, which are located in the optical paths of the two light beams, and the slight difference in frequency Δf is thereby caused to occur between the two light beams.

Of the two modulated light beams, the signal light beam passes through the beam splitter 21b and impinges upon the eyeball 100.

The signal light beam impinging upon the eyeball 100 is classified into four light beams described in ①, ②, ③, and ④ below.

① The light beam reflected from the interface between air and the cornea 110.

② The light beam reflected from the interface between the cornea 110 and the anterior aqueous chamber 120.

③ The light beam reflected from the interface between the anterior aqueous chamber 120 and the crystalline lens 130.

④ The light beam passing through the crystalline lens 130.

Of these light beams, the light beams described in ①, ②, and ③ emanate as backward scattered light beams from the eyeball 100 reversely from the direction of travel of the incident signal light beam.

Each of the backward scattered light beams emanating from the eyeball 100 is reflected by the beam splitter 21b and passes through the beam splitter 21d.

The reference light beam having been modulated is reflected by the beam splitter 21c and impinges upon the mirror 27. The reference light beam is then reflected from the mirror 27 and again impinges upon the beam splitter 21c. The reference light beam passes through the beam splitter 21c and is reflected by the beam splitter 21d.

At this time, the length of the optical path, along which the reference light beam travels before arriving at the beam splitter 21d, can be changed by moving the mirror 27 in its optical axis direction (along one of the directions indicated by the double headed arrow X).

The reference light beam, the signal light beam impinging upon the eyeball 100, and the backward scattered light beams emanating from the eyeball 100 are the low coherence light beams having a short coherence length. Therefore, of the three backward scattered light beams described above, only the backward scattered light beam, which satisfies the condition such that the sum of the distance of passage as the signal light beam and the distance of passage as the backward scattered light beam to the arrival at the beam splitter 21d may be approximately equal to the distance of passage of the reference light beam to the arrival at the beam splitter 21d, interferes with the reference light beam. As a result, a beat signal occurs, the intensity of which repeatedly becomes high and low at a frequency equal to the difference in frequency (Δf) between the backward scattered light beam and the reference light beam interfering with each other.

Specifically, the interference occurs when the conditions described below are satisfied.

(1) When the backward scattered light beam described in ① and the reference light beam interfere with each other:

The sum of the distance between the beam splitter 21a and the beam splitter 21b, two times the distance between the beam splitter 21b and the air/cornea interface, and the distance between the beam splitter 21b and the beam splitter 21d is approximately equal to the sum of the distance between the beam splitter 21a and the beam splitter 21c, two times the distance between the beam splitter 21c and the mirror 27, and the distance between the beam splitter 21c and the beam splitter 21d.

(2) When the backward scattered light beam described in ② and the reference light beam interfere with each other:

The sum of the distance between the beam splitter 21a and the beam splitter 21b, two times the distance between the beam splitter 21b and the cornea/anterior aqueous chamber interface, and the distance between the beam splitter 21b and the beam splitter 21d is approximately equal to the sum of the distance between the beam splitter 21a and the beam splitter 21c, two times the distance between the beam splitter 21c and the mirror 27, and the distance between the beam splitter 21c and the beam splitter 21d.

(3) When the backward scattered light beam described in ③ and the reference light beam interfere with each other:

The sum of the distance between the beam splitter 21a and the beam splitter 21b, two times the distance between the beam splitter 21b and the anterior aqueous chamber/ crystalline lens interface, and the distance between the beam splitter 21b and the beam splitter 21d is approximately equal to the sum of the distance between the beam splitter 21a and the beam splitter 21c, two times the distance between the beam splitter 21c and the mirror 27, and the distance between the beam splitter 21c and the beam splitter 21d.

Therefore, the mirror 27, which is firstly located at a position close to the beam splitter 21c, is moved little by little in the direction heading away from the beam splitter 21c and to a position, at which the beat signal due to the interference of the backward scattered light beam of the signal light beam, the backward scattered light beam coming from the interface between air and the cornea 110, and the reference light beam with each other is detected with the photodetector 28.

When the mirror 27 is further moved in the direction heading away from the beam splitter 21c, the occurrence of the beat signal ceases. When the mirror 27 is moved even further, a beat signal is again detected by the photodetector 28. The second beat signal is caused to occur by the interference of the backward scattered light beam (hereinbelow referred to as the first backward scattered light beam) of the signal light beam, the first backward scattered light beam coming from the interface between the cornea 110 and the anterior aqueous chamber 120, and the reference light beam with each other. The second beat signal occurs when the mirror 27 has been moved by a length equal to the thickness of the cornea 110 from the position, at which the first beat signal was detected.

The beat signal occurring due to the interference of the first backward scattered light beam and the reference light beam with each other is taken as a first interference light beam, and its intensity $B_{R2}$ is detected by the photodetector 28.

When the mirror 27 is further moved in the direction heading away from the beam splitter 21c, the occurrence of the beat signal ceases. When the mirror 27 is moved even further, a third beat signal is detected by the photodetector 28. The third beat signal is caused to occur by the interference of the backward scattered light beam (hereinbelow referred to as the second backward scattered light beam) of the signal light beam, the second backward scattered light beam coming from the interface between the anterior aqueous chamber 120 and the crystalline lens 130, and the reference light beam with each other. The third beat signal occurs when the mirror 27 has been moved by a length equal to the thickness of the anterior aqueous chamber 120 from the position, at which the second beat signal was detected.

The beat signal occurring due to the interference of the second backward scattered light beam and the reference light beam with each other is taken as a second interference light beam, and its intensity $B_{R3}$ is detected by the photodetector 28.

The intensities $B_{R2}$ and $B_{R3}$ of the two beat signals having been obtained in the manner described above are converted into electric signals, and the electric signals are fed into the heterodyne operation means 29. The heterodyne operation means 29 calculates the intensity $I_{R2}$ of the first backward scattered light beam and the intensity $I_{R3}$ of the second backward scattered light beam from the received electric signals.

Specifically, the intensity $B_{R2}$ of the first interference light beam is the square root of the product of the intensity $I_{R2}$ of the first backward scattered light beam and the intensity of the reference light beam. Also, the intensity $B_{R3}$ of the second interference light beam is the square root of the product of the intensity $I_{R3}$ of the second backward scattered light beam and the intensity of the reference lightbeam. As the intensity the reference light beam, a value having been measured previously may be employed. As a result, the intensity $I_{R2}$ of the first backward scattered light beam and the intensity $I_{R3}$ of the second backward scattered light beam can be calculated.

How the light absorption characteristics analyzing means 30 operates will be described hereinbelow with reference to FIG. 2.

As illustrated in FIG. 2, the intensity of the signal light beam serving as the incident light beam impinging upon the eyeball 100 is represented by $I_0$. The reflectivity of the interface between air and the cornea 110 is represented by $R_1$, the reflectivity of the interface between the cornea 110 and the anterior aqueous chamber 120 is represented by $R_2$, and the reflectivity of the interface between the anterior aqueous chamber 120 and the crystalline lens 130 is represented by $R_3$. Also, the optical absorbance of the cornea 110 with respect to the incident light beam along one way of the optical path is represented by $\alpha_1$, and the optical absorbance of the anterior aqueous chamber (the aqueous humor) 120 with respect to the incident light beam along one way of the optical path is represented by $\alpha_2$. In such cases, the intensity $I_{R2}$ of the first backward scattered light beam and the intensity $I_{R3}$ of the second backward scattered light beam may be represented by Formulas (1) and (2) shown below.

$$I_{R2}=I_0(1-R_1)^2 R_2(1-\alpha_1)^2 \tag{1}$$

$$I_{R3}=I_0(1-R_1)^2(1-R_2)^2 R_3(1-\alpha_1)^2(1-\alpha_2)^2 \tag{2}$$

As will be understood from FIG. 2 and Formula (2), the intensity $I_{R3}$ of the second backward scattered light beam depends upon both of the optical absorbance ($\alpha_2$ of the aqueous humor 120 and the optical absorbance a of the cornea 110.

The light absorption characteristics analyzing means 30 calculates the ratio ($I_{R3}/I_{R2}$) of the intensity $I_{R3}$ of the second backward scattered light beam to the intensity $I_{R2}$ of the first backward scattered light beam. The calculation is made with Formula (3) shown below.

$$I_{R3}/I_{R2}=(R_3/R_2)(1-R_2)^2(1-\alpha_2)^2 \tag{3}$$

The values of $I_{R3}$ and $I_{R2}$ have been calculated accurately by the heterodyne operation means 29, and $R_3$ and $R_2$ are already known. Therefore, the optical absorbance $\alpha_2$ of the aqueous humor 120 alone can be calculated from them.

Besides glucose, the aqueous humor 120 contains a plurality of other constituents, such as NaCl. Therefore, the concentration of glucose in the aqueous humor 120 cannot be determined only from the optical absorbance $\alpha_2$ of the aqueous humor 120, which has been obtained with the incident light beam having the wavelength $\lambda 1$. [The optical absorbance $\alpha_2$ of the aqueous humor 120, which has been obtained with the incident light beam having the wavelength $\lambda 1$, will hereinbelow be represented by $\alpha_2$ (1).]

Therefore, secondly, the second SLD 11b radiates out the low coherence light beam, which has a center wavelength of $\lambda 2$. At this time, the other SLDs, including the first SLD 11a, do not radiate out the light beams.

As in the low coherence light beam having the wavelength of $\lambda 1$ described above, the low coherence light beam having a center wavelength of $\lambda 2$, which has been radiated out of the SLD 11b, is split by the first beam splitter 21a, which is located in the optical path, into the signal light beam and the reference light beam. The signal light beam impinges upon the eyeball 100, and the reference light beam is reflected by the mirror 27. Interference light beams are thereby obtained at the beam splitter 21d. By the same effects of the photodetector 28, the heterodyne operation means 29, and the light absorption characteristics analyzing means 30 as those described above, an optical absorbance $\alpha_2$ (2) of the aqueous humor 120 with respect to the second incident light beam having the center wavelength of $\lambda 2$ is obtained.

The same operation as that described above is repeated with respect to the SLD 11c, ..., SLD 11x. In this manner, the optical absorbances $\alpha_2$ (1), $\alpha_2$ (2), ..., $\alpha_2$ (n) of the aqueous humor 120 with respect to a plurality of the incident light beams having the wavelengths of $\lambda 1, \lambda 2, \ldots, \lambda n$ can be obtained.

The information representing the optical absorbances $\alpha_2$ (1), $\alpha_2$ (2), ..., $\alpha_2$ (n), which have thus been obtained with respect to the incident light beams having different wavelengths, is fed into the glucose concentration calculating means 40. The glucose concentration calculating means 40 determines the concentration of glucose in the aqueous humor 120, which contains a plurality of constituents, from the plurality of the optical absorbances by utilizing the known near-infrared spectroscopy including the multivariate analysis.

In this manner, with this embodiment of the glucose concentration measuring apparatus in accordance with the present invention, the concentration of glucose in the aqueous humor can be measured non-invasively and accurately.

For each patient, the correlation between the concentrations of glucose in the aqueous humor, which have thus been obtained with the glucose concentration measuring apparatus in accordance with the present invention, and the concentrations of glucose in the blood, which have been obtained invasively in accordance with the conventional procedure, is prepared as, for example, a conversion table. The information representing the conversion table is stored in a memory 52 of an aqueous humor glucose concentration-to-blood glucose concentration converting means 50. When information representing the concentration of glucose in the aqueous humor of a certain patient is fed from the glucose concentration measuring apparatus described above into the aqueous humor glucose concentration-to-blood glucose concentration converting means 50, a converting operation means 51 of the aqueous humor glucose concentration-to-blood glucose concentration converting means 50 refers to the conversion table, which is stored in the memory 52, and feeds out the information representing the concentration of glucose in the blood, which corresponds to the concentration of glucose in the aqueous humor of the patient. In such cases, after the conversion table is prepared, the concentration of glucose in the aqueous humor is measured non-invasively with the glucose concentration measuring apparatus described above, and the corresponding concentration of glucose in the blood can be calculated from the measured concentration of glucose in the aqueous humor and the conversion table. Accordingly, the concentration of glucose in the blood can be determined non-invasively.

In the embodiments, which will be described later, the aqueous humor glucose concentration-to-blood glucose concentration converting means 50 may be provided, and the same effects as those described above can thereby be obtained.

In the aforesaid embodiment of the glucose concentration measuring apparatus in accordance with the present invention, the light source device 10 comprising a plurality of the light sources 11a, 11b, ..., 11x, which radiate out the light beams of different wavelength bands, is employed.

Figure 4A:
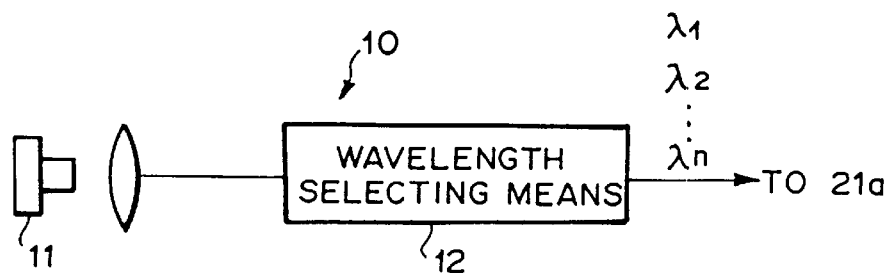
FIG. 4A is a schematic view showing a different example of a light source device, which may be employed in the embodiment of FIG. 3.

However, the first glucose concentration measuring method and apparatus in accordance with the present invention are not limited to the use of a plurality of light sources. For example, as illustrated in FIG. 4A, the light source device 10 maybe constituted of a single light source 11 for radiating out low coherence light, which is of a wide emission wavelength band containing all of the wavelength bands of the aforesaid low coherence light beams, and a wavelength selecting means 12 for selecting each of the aforesaid low coherence light beams (which is of a predetermined wavelength band) from the low coherence light, which is of the wide emission wavelength band and has been radiated out of the light source 11.

The aforesaid embodiment is designed for non-invasively determining the concentration of glucose in the blood by utilizing the non-invasively measured concentration of glucose in the aqueous humor. The aforesaid embodiment also serves as an embodiment of the fourth glucose concentration measuring method and apparatus in accordance with the present invention.

Figure 5:
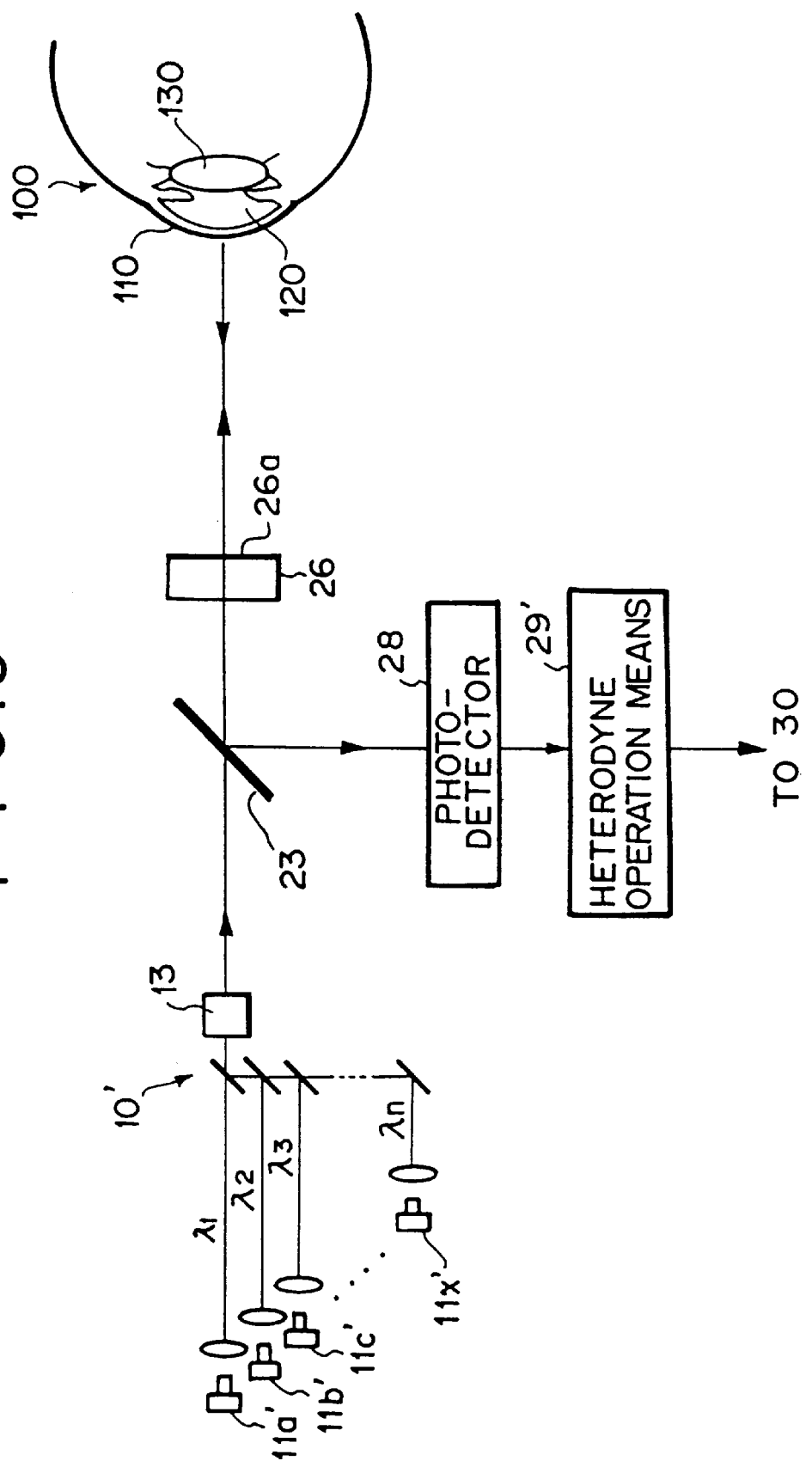
FIG. 5 is a schematic view showing an embodiment of an apparatus for carrying out the second glucose concentration measuring method in accordance with the present invention.

FIG. 5 shows an embodiment of an apparatus for carrying out the second glucose concentration measuring method in accordance with the present invention.

Figure 6:
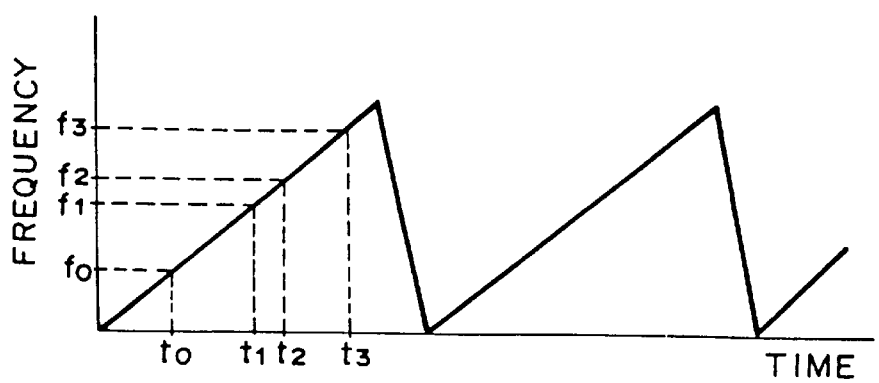
FIG. 6 is a graph showing a frequency sweeping pattern.

The constitution of the glucose concentration measuring apparatus shown in FIG. 5 is basically similar to the constitution of FIG. 1. In the glucose concentration measuring apparatus shown in FIG. 5, a light source device 10' is employed in lieu of the light source device 10 shown in FIG. 1. The light source device 10' comprises a light source 11a' for radiating out a laser beam having a wavelength $\lambda 1$, a light source 11b' for radiating out a laser beam having a wavelength $\lambda 2$, ..., a light source 11x' for radiating out a laser beam having a wavelength $\lambda n$, and a frequency sweep means 13, which receives each of the laser beams and temporally sweeps the frequency of the laser beam in a sawtooth-like form with a predetermined band as illustrated in FIG. 6. In this embodiment, the laser beams are employed as coherent light beams. However, in the second glucose concentration measuring method and apparatus in accordance with the present invention, any of other kinds of coherent light beams may be employed.

Also, in the glucose concentration measuring apparatus of FIG. 5, the optical heterodyne measurement means 20 shown in FIG. 1 comprises a beam splitter 23, a reflection plate 26 serving as an optical path splitting means and a wavefront matching means, a photodetector 28, and a heterodyne operation means 29' for calculating the intensity of a backward scattered light beam from the intensity of an interference light beam.

The laser beam, which has been radiated out of the light source device 10' and the frequency of which has been swept by the frequency sweep means 13, passes through the beam splitter 23 and impinges upon the eyeball 100. The reflection plate 26 matches a wave front of a backward scattered light beam of the laser beam having been irradiated to the eyeball 100, the backward scattered light beam coming from each reflection surface, and a wave front of a laser beam (a reference light beam) radiated out of the light source device 10' with a time lag behind the aforesaid laser beam having been irradiated to the eyeball 100, the laser beam (the reference light beam) having a slight difference in frequency with respect to the backward scattered light beam and having been reflected from a reflection surface 26a of the reflectionplate 26, with each other. An interference light beam is caused to occur by the wavefront matching.

The photodetector 28 detects the intensity of the interference light beam, which has been caused to occur by the matching of the wave front of the backward scattered light beam and the wave front of the laser beam (the reference light beam) radiated out of the light source device 10' with a time lag behind the aforesaid laser beam having been irradiated to the eyeball 100, the laser beam (the reference light beam) arriving at the reflection plate 26 at the same time as the backward scattered light beam and reflected.

The heterodyne operation means 29' calculates the intensity of the backward scattered light beam from the intensity of the interference light beam, which intensity has been detected by the photodetector 28, by utilizing the optical heterodyne backward scattering measurement technique.

Though not shown in FIG. 5, this embodiment of the glucose concentration measuring apparatus is also provided with the light absorption characteristics analyzing means 30 and the glucose concentration calculating means 40, which are shown in FIGS. 1 and 3. The effects of the light absorption characteristics analyzing means 30 and the glucose concentration calculating means 40 are the same as those described above with reference to FIG. 1 or FIG. 3.

How this embodiment of the glucose concentration measuring apparatus operates will be described hereinbelow.

Firstly, the laser beam having a wavelength $\lambda 1$ is produced by the light source 11a. The frequency of the laser beam is swept by the frequency sweep means 13 of the light source device 10', and the laser beam is radiated out of the light source device 10'. As illustrated in FIG. 6, the frequency of the laser beam, which is radiated out of the light source device 10' at the time $t_0$, is represented by $f_0$.

The light beam (the laser beam) having the frequency $f_0$, which has been radiated out of the light source device 10', passes through the beam splitter 23, which is located in the optical path, and impinges upon the reflection plate 26. The reflection surface 26a of the reflection plate 26 is formed as a semi-transparent mirror. Therefore, the reflection surface 26a reflects a portion of the incident light beam and allows the remainder of the incident light beam to pass therethrough. The reflected light beam serves as the reference light beam, and the light beam having passed through the reflection surface 26a serves as the signal light beam.

Therefore, a portion of the light beam having the frequency $f_0$ is reflected from the reflection surface 26a, and the remainder of the light beam passes through the reflection surface 26a.

The light beam having the frequency $f_0$, which has passed through the reflection surface 26a, impinges upon the eyeball 100. The light beam impinging upon the eyeball 100 is classified into four light beams described in (①, ②, ③, and ④) below.

① The light beam reflected from the interface between air and the cornea 110.

② The light beam reflected from the interface between the cornea 110 and the anterior aqueous chamber 120.

③ The light beam reflected from the interface between the anterior aqueous chamber 120 and the crystalline lens 130.

④ The light beam passing through the crystalline lens 130.

Of these light beams, the light beams described in ①, ②, and ③ emanate as backward scattered light beams from the eyeball 100 reversely from the direction of travel of the incident light beam and arrive at the reflection plate 26.

The length of the optical path of the signal light beam having the frequency $f_0$, which has passed through the reflection surface 26a of the reflection plate 26, the signal light beam impinging upon the eyeball 100 and again arriving at the reflection surface 26a as the backward scattered light beam, can be classified into those described below.

(1) As for the backward scattered light beam described in ① above: Two times the distance from the reflection surface 26a of the reflection plate 26 to the interface between air and the cornea 110.

(2) As for the backward scattered light beam described in ② above: Two times the sum of the distance from the reflection surface 26a of the reflection plate 26 to the interface between air and the cornea 110 and the distance from the interface between air and the cornea 110 to the interface between the cornea 110 and the anterior aqueous chamber 120.

(3) As for the backward scattered light beam described in ③ above: Two times the sum of the distance from the reflection surface 26a of the reflection plate 26 to the interface between air and the cornea 110, the distance from the interface between air and the cornea 110 to the interface between the cornea 110 and the anterior aqueous chamber 120, and the distance from the interface between the cornea 110 and the anterior aqueous chamber 120 to the interface between the anterior aqueous chamber 120 and the crystalline lens 130.

Therefore, the lengths of the optical paths of the backward scattered light beams (including the length of the optical path to the impingement upon the eyeball 100) are different from one another. As a result, the backward scattered light beams arrive at the reflection surface 26a of the reflection plate 26 with a difference in time corresponding to the difference in optical path length.

The laser beam, the frequency of which is swept temporarily, is successively radiated out of the light source device 10' and successively arrives at the reflection plate 26.

As a result, at the reflection surface 26a of the reflection plate 26, for example, the backward scattered light beam described in ① above (having the frequency $f_0$) meets with the light beam having a frequency $f_1$, which has been radiated out of the light source device 10' at the time $t_1$, (as illustrated in FIG. 6), and the wave fronts of the two light beams are matched with each other. Therefore, a beat signal of the interference light beam, which is caused to occur by the wavefront matching, is obtained such that the intensity of the beat signal may repeatedly becomes high and low at a frequency equal to the difference $(f_1-f_0)$ between the frequencies of the two light beams subjected to the wavefront matching.

Also, at the reflection surface 26a of the reflection plate 26, the backward scattered light beam described in ② above (having the frequency $f_0$) meets with the light beam having a frequency $f_2$, which has been radiated out of the light source device 10' at the time $t_2$, and the wave fronts of the two light beams are matched with each other. Therefore, the frequency of a beat signal of the interference light beam, which is caused to occur by the wavefront matching, is equal to the difference $(f_2-f_0)$ between the frequencies of the two light beams subjected to the wavefront matching.

Further, at the reflection surface 26a of the reflection plate 26, the backward scattered light beam described in ③ above (having the frequency $f_0$) meets with the light beam having a frequency $f_3$, which has been radiated out of the light source device 10' at the time $t_3$, and the wave fronts of the two light beams are matched with each other. Therefore, the frequency of a beat signal of the interference light beam, which is caused to occur by the wavefront matching, is equal to the difference $(f_3-f_0)$ between the frequencies of the two light beams subjected to the wavefront matching.

From the light source device 10', the laser beam, the frequency of which changes with the passage of time, is successively radiated out. However, since the differences among the aforesaid optical path lengths are invariable, the frequencies of the beat signals caused to occur by the interference with the respective backward scattered light beams are kept constant.

The light beam, which is obtained from the interference of each backward scattered light beam at the reflection surface 26a of the reflection plate 26, is reflected from the beam splitter 23 and impinges upon the photodetector 28.

The photodetector 28 detects the intensity of the light beam composed of the three beat signals, the intensities of which repeatedly become high and low at different frequencies. The photodetector 28 converts the intensity into an electric signal. The electric signal is fed into the heterodyne operation means 29'.

The heterodyne operation means 29' separates the beat signals obtained with the respective backward scattered light beams from one another in accordance with the received electric signal and calculates the intensity of each backward scattered light beam from each of the beat signals separated from one another.

As for the separation of the beat signals obtained with the respective backward scattered light beams from one another, if the thicknesses of the cornea 110 and the anterior aqueous chamber 120 along the optical axis direction are known, the differences in frequency among the beat signals obtained with the respective backward scattered light beams can be calculated easily from the difference in light passage time according to the thicknesses and the frequency sweep speed. Even if the thicknesses of the cornea 110 and the anterior aqueous chamber 120 along the optical axis direction are not known, a known frequency analysis may be made with respect to the combined beat signal, and the frequencies of the beat signals obtained with the respective backward scattered light beams can be calculated easily.

The information representing the intensities of the respective backward scattered light beams, the intensities having been calculated by the heterodyne operation means 29' in the manner described above, is fed into the light absorption characteristics analyzing means 30.

The same operation as that described above is repeated with respect to the light sources $11b'$, ..., $11x'$ In this manner, the optical absorbances $\alpha_2$ (1), $\alpha_2$ (2), ..., $\alpha_2$ (n) of the aqueous humor 120 with respect to a plurality of the incident light beams having different wavelengths can be obtained. The information representing the optical absorbances $\alpha_2$ (1), $\alpha_2$ (2), ..., $\alpha_2$ (n), which have thus been obtained with respect to the incident light beams having different wavelengths, is fed into the glucose concentration calculating means 40. The glucose concentration calculating means 40 determines the concentration of glucose in the aqueous humor 120, which contains a plurality of constituents, from the plurality of the optical absorbances by utilizing the known near infrared spectroscopy including the multivariate analysis.

In this manner, with this embodiment of the glucose concentration measuring apparatus in accordance with the present invention, the concentration of glucose in the aqueous humor can be measured non-invasively and accurately.

Figure 4B:
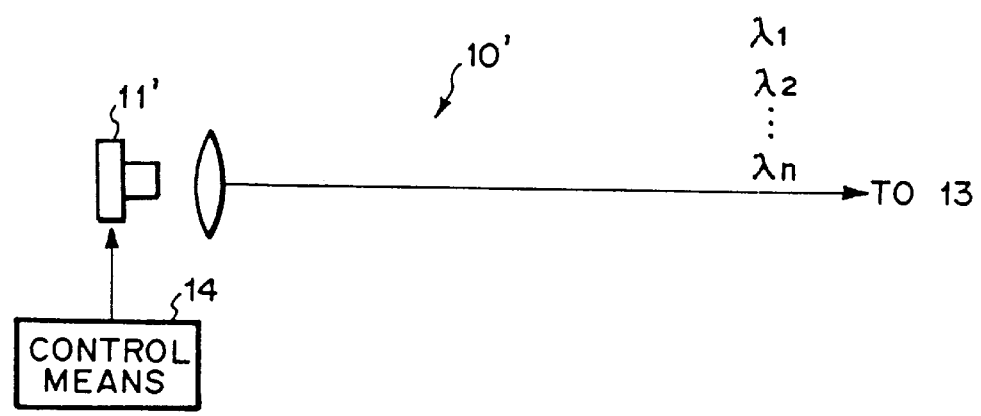
FIG. 4B is a schematic view showing a different example of a light source device, which may be employed in an embodiment of FIG. 5.

In this embodiment of FIG. 5, the light source device 10' comprising a plurality of the light sources 11a, 11b', ..., 11x', which radiate out the coherent lightbeams, is employed. However, the second glucose concentration measuring method and apparatus in accordance with the present invention are not limited to the use of a plurality of light sources. For example, as illustrated in FIG. 4B, the light source device 10' may be constituted of a single light source 11' capable of selectively radiating out each of a plurality of coherent light beams, and a control means 14 for controlling the light source 11' such that the light source 11' may selectively radiate out one of the plurality of the coherent light beams.

FIG. 7 shows an embodiment of an apparatus for carrying out the third glucose concentration measuring method in accordance with the present invention.

With reference to FIG. 7, the glucose concentration measuring apparatus comprises a light source device 10" for radiating out a plurality of ultrashort pulsed light beams, which have different wavelengths. The light source device 10" is provided with a Ti:sapphire laser beam source (hereinbelow referred to simply as the light source) 11a" for radiating out an ultrashort pulsed light beam having a wavelength $\lambda 1$, a light source 11b" for radiating out an ultrashort pulsed light beam having a wavelength $\lambda 2$, ..., a light source 11x" for radiating out an ultrashort pulsed light beam having awavelength $\lambda n$. The glucose concentration measuring apparatus also comprises an optical time-domain backward scattering measurement means 60 for irradiating the ultrashort pulsed light beam to the eyeball 100, and carrying out time series measurement of each of an intensity of a first backward scattered light beam of the ultrashort pulsed light beam, the first backward scattered light beam coming from an interface between the cornea 110 and the anterior aqueous chamber 120 of the eyeball 100, and an intensity of a second backward scattered light beam of the ultrashort pulsed light beam, the second backward scattered light beam coming from an interface between the anterior aqueous chamber 120 and the crystalline lens 130 of the eyeball 100. The optical time-domain backward scattering measurement means 60 contain a photodetector, such as a streak camera. The glucose concentration measuring apparatus further comprises a light absorption characteristics analyzing means 30 for obtaining light absorption characteristics of constituents of the aqueous humor, which fills the anterior aqueous chamber 120, from the intensity of the first backward scattered light beam and the intensity of the second backward scattered light beam. The glucose concentration measuring apparatus still further comprises a glucose concentration calculating means 40 for calculating a concentration of glucose in the constituents of the aqueous humor from the light absorption characteristics, which have been obtained with respect to the plurality of the ultrashort pulsed light beams having different wavelengths.

The pulsed light beam is emitted for a very short time on the order of, for example, femtoseconds to picoseconds.

Figure 8:
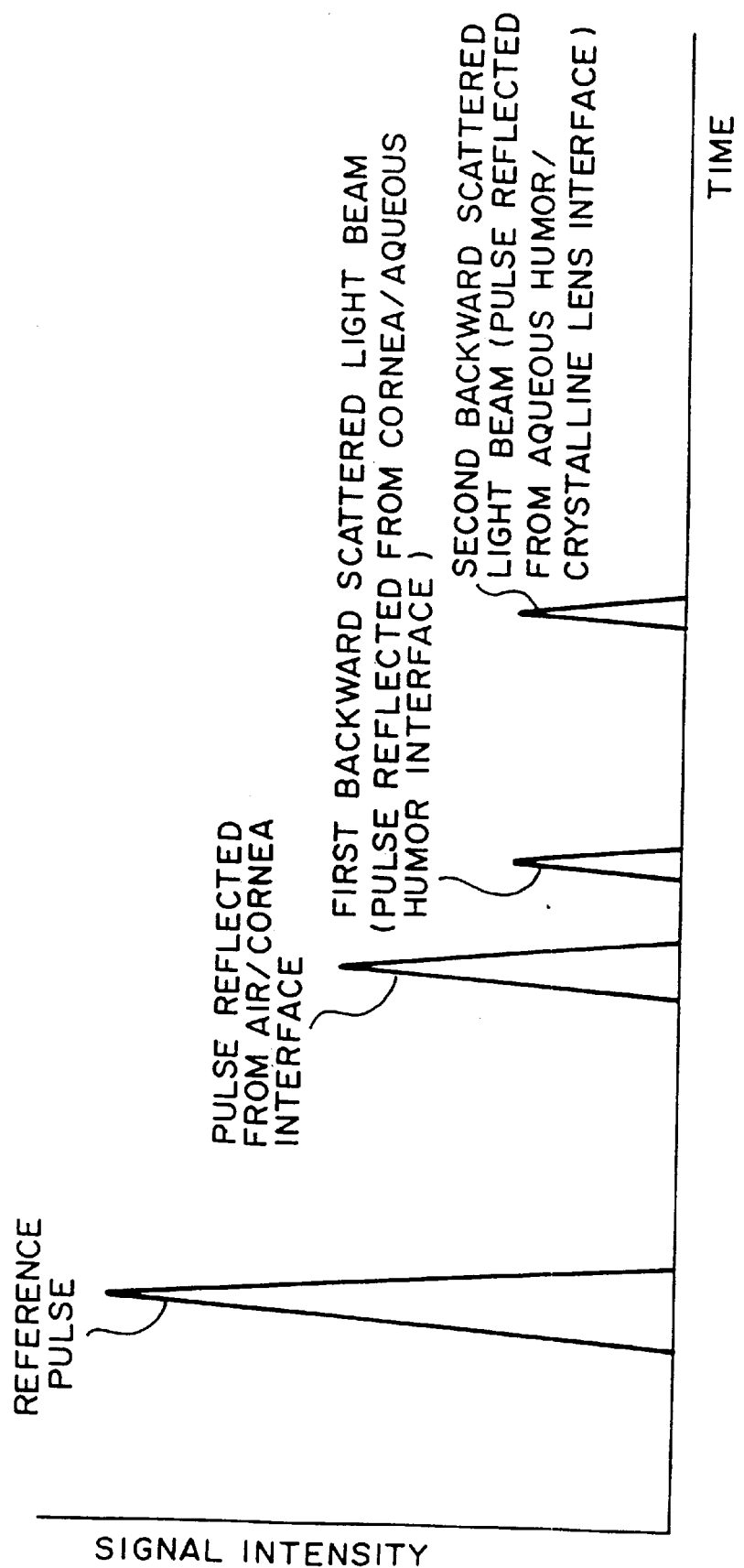
FIG. 8 is a graph showing intensities of light beams detected with a photodetector capable of effecting time resolution.

The optical time-domain backward scattering measurement means 60 comprises a beam splitter 61 for splitting the ultrashort pulsed light beam, which has been radiated out of the light source device 10" , into a signal light beam irradiated to the eyeball 100 and a reference light beam to be utilized in timing the detection of each backward scattered light beam of the incident light beam, the backward scattered light beam emanating from the eyeball 100. The optical time-domain backward scattering measurement means 60 also comprises mirrors 62, 62, 62 for guiding the reference light beam, and a photodetector 63 capable of measuring the intensities of the respective backward scattered light beams of the incident light beam, the backward scattered light beams emanating from the eyeball 100, such that the intensities may be temporally separated from one another as illustrated in FIG. 8. The photodetector 63 may be constituted of a streak camera, or the like. The optical time-domain backward scattering measurement means 60 further comprises a aqueous humor transmittance operation means 64 for calculating the amount of each backward scattered light beam by integrating the intensity of each backward scattered light beam, which has been temporally separated and detected, with respect to time.

The reference light beam is utilized for the timing of the detection of each backward scattered light beam. The reference light beam is also utilized to monitor the amount of the signal light beam impinging upon the eyeball 100. The reference light beam is introduced into the photodetector 63.

How this embodiment of FIG. 7 operates will be described hereinbelow.

Firstly, the light source 11a" radiates out the ultrashort pulsed light beam having the wavelength $\lambda 1$. The ultrashort pulsed light beam enters into the optical time-domain backward scattering measurement means 60 and is split by the beam splitter 61 into the signal light beam and the reference light beam.

Of the split light beams, the signal light beam impinges upon the eyeball 100. As described above with reference to the aforesaid embodiments, the signal light beam impinging upon the eyeball 100 is classified into the four light beams. Of the four classified light beams, the light beams described in ①, ②, and ③ below emanate as the backward scattered light beams from the eyeball 100.

① The light beam reflected from the interface between air and the cornea 110.

② The light beam reflected from the interface between the cornea 110 and the anterior aqueous chamber 120.

③ The light beam reflected from the interface between the anterior aqueous chamber 120 and the crystalline lens 130.

The depths of the reflection planes, from which the respective backward scattered light beams are reflected, the depths being taken with respect to the direction of incidence of the signal light beam, are different from one another. Therefore, the timings, with which the respective backward scattered light beams emanate from the eyeball 100, are different from one another. Specifically, the backward scattered light beam described in ①, the backward scattered light beam described in ②, and the backward scattered light beam described in ③, emanate in this order from the eyeball 100. Also, since the backward scattered light beams are the reflected light of the incident signal light beam, they are the ultrashort pulsed light beams. The emission period of the ultrashort pulsed light beams is shorter than the difference in time for passage corresponding to the aforesaid difference in depth of reflection plane. Therefore, the backward scattered light beams emanate from the eyeball 100 one after another such that they may be separated perfectly.

Each of the backward scattered light beams, which emanate from the eyeball 100 one after another, is reflected from the beam splitter 61 and impinges upon the photodetector 63 capable of effecting time resolution.

Before each backward scattered light beam impinges upon the photodetector 63, the reference light beam, which has been reflected from the beam splitter 61 and guided by the mirrors 62, 62, 62, enters into the photodetector 63. The reference light beam serves as a trigger for the timing of the detection carried out by the photodetector 63. The intensity of the reference light beam is detected, and the intensities of the backward scattered light beams are detected respectively.

FIG. 8 is a graph showing the intensity of the reference light beam and the intensities of backward scattered light beams, which are time-resolved and detected by the photodetector 63 on the time series basis.

The photodetector 63 converts the detected intensity of each light beam into an electric signal. The electric signal is fed into the aqueous humor transmittance operation means 64.

The aqueous humor transmittance operation means 64 integrates the received electric signal, which corresponds to the intensity of each light beam, with respect to time and thereby calculates the amount of each light beam. The information representing the thus calculated amount of each light beam is fed into the light absorption characteristics analyzing means 30. In the same manner as that in the aforesaid embodiments, the light absorption characteristics analyzing means 30 calculates the optical absorbance of the aqueous humor 120 in accordance with the amount of each light beam.

The same operation as that described above is repeated with respect to the ultrashort pulsed light beams having different wavelengths, which are radiated out of the light source device 10", i.e. by utilizing the plurality of the light sources 11a", 11b", . . . , 11x", which radiate out the pulsed light beams having different wavelengths, one after another. In this manner, the optical absorbances of the aqueous humor 120 with respect to a plurality of the incident light beams having different wavelengths can be obtained.

The information representing the optical absorbances, which have thus been obtained with respect to the incident light beams having different wavelengths, is fed into the glucose concentration calculating means 40. The glucose concentration calculating means 40 determines the concentration of glucose in the aqueous humor 120, which contains a plurality of constituents, from the plurality of the optical absorbances by utilizing the known near-infrared spectroscopy including the multivariate analysis.

In this manner, with this embodiment of the glucose concentration measuring apparatus in accordance with the present invention, the concentration of glucose in the aqueous humor can be measured non-invasively and accurately.

In this embodiment of FIG. 7, the light source device 10" comprising a plurality of the light sources 11a", 11b", . . . , 11x", which radiate out the ultrashort pulsed light beams having different wavelengths, is employed. However, the third glucose concentration measuring method and apparatus in accordance with the present invention are not limited to the use of a plurality of light sources. For example, as in the light source device 10' in the aforesaid embodiment of the second glucose concentration measuring method and apparatus, the light source device 10" may be constituted of a single light source capable of selectively radiating out each of a plurality of ultrashort pulsed light beams, and a control means for controlling the light source such that the light source may selectively radiate out one of the plurality of the ultrashort pulsed light beams.

What is claimed is:

1. A glucose concentration measuring method, comprising the steps of:

i) irradiating an ultrashort pulsed light beam, which has been radiated out of a predetermined light source, to the eyeball, ii) measuring each of an intensity of a first backward scattered light beam of said ultrashort pulsed light beam, said first backward scattered light beam coming from an interface between the cornea and the anterior aqueous chamber of the eyeball, and an intensity of a second backward scattered light beam of said ultrashort pulsed light beam, said second backward scattered light beam coming from an interface between the anterior aqueous chamber and the crystalline lens of the eyeball, iii) obtaining light absorption characteristics of constituents of the aqueous humor, which fills the anterior aqueous chamber, from the intensity of said first backward scattered light beam and the intensity of said second backward scattered light beam, iv) obtaining light absorption characteristics of the constituents of the aqueous humor with respect to each of a plurality of other ultrashort pulsed light beams, which have wavelengths different from the wavelength of said ultrashort pulsed light beam, by repeating steps i)–iii) with each of the plurality of other ultrashort pulsed light beams, and v) calculating a concentration of glucose in the constituents of the aqueous humor from the light absorption characteristics, which have been obtained with respect to the plurality of said ultrashort pulsed light beams having different wavelengths.

2. A method as defined in claim 1 wherein said ultrashort pulsed light beams are selectively radiated out of a single light source.

3. A method as defined in claim 1 wherein each of said ultrashort pulsed light beams is radiated out of one of a plurality of different light sources.

4. A glucose concentration measuring method, comprising the steps of:

determining concentrations of glucose in the constituents of the aqueous humor, which with a method as defined in claim 1, and invasively measuring the corresponding concentrations of glucose in the blood, correlating the concentrations of glucose in the constituents of the aqueous humor and the concentrations of glucose in the blood, and non-invasively determining a concentration of glucose in the blood from a concentration of glucose in the constituents of the aqueous humor, which concentration is newly measured with a method as defined in claim 1, and said correlation.

5. A glucose concentration measuring apparatus, comprising:

i) a light source device for radiating out a plurality of ultrashort pulsed light beams, which have different wavelengths, ii) an optical time-domain backward scattering measurement means for irradiating said plurality of ultrashort pulsed light beams to the eyeball, and carrying out time series measurement of each of an intensity of a first backward scattered light beam of said ultrashort pulsed light beam, said first backward scattered light beam coming from an interface between the cornea and the anterior aqueous chamber of the eyeball, and an intensity of a second backward scattered light beam of said ultrashort pulsed light beam, said second backward scattered light beam coming from an interface between the anterior aqueous chamber and the crystalline lens of the eyeball, iii) a light absorption characteristics analyzing means for obtaining light absorption characteristics of constituents of the aqueous humor, which fills the anterior aqueous chamber, from the intensity of said first backward scattered light beam and the intensity of said second backward scattered light beam, and iv) a glucose concentration calculating means for calculating a concentration of glucose in the constituents of the aqueous humor from the light absorption characteristics, which have been obtained with respect to the plurality of said ultrashort pulsed light beams having different wavelengths.

6. An apparatus as defined in claim 5 wherein said light source device comprises a single light source capable of selectively radiating out each of the plurality of said ultrashort pulsed light beams, and a control means for controlling said light source such that said light source may selectively radiate out one of the plurality of said ultrashort pulsed light beams.

7. An apparatus as defined in claim 5 wherein said light source device comprises a plurality of light sources, each of which radiates out one of said ultrashort pulsed light beams.

8. A glucose concentration measuring apparatus, as defined in claim 5, further comprising a table representing correlation between concentrations of glucose in the constituents of the aqueous humor and concentrations of glucose in the blood, which have been measured previously.

* * * * *